United States Patent [19]
Walkotten

[11] 4,038,875
[45] Aug. 2, 1977

[54] CRYOGENIC SEDIMENT SAMPLER

[75] Inventor: William J. Walkotten, Juneau, Alaska

[73] Assignee: The United States of America as represented by the Secretary of Agriculture, Washington, D.C.

[21] Appl. No.: 687,489

[22] Filed: May 18, 1976

[51] Int. Cl.² .......................... F25D 3/14; G01N 1/08
[52] U.S. Cl. ........................................ 73/425; 62/293; 73/421 R
[58] Field of Search .................... 73/425, 425.2, 425.4, 73/421 R, 64; 62/476, 293

[56] References Cited
U.S. PATENT DOCUMENTS

| | | | |
|---|---|---|---|
| 2,305,367 | 12/1942 | Webb | 62/293 |
| 2,672,032 | 3/1954 | Towse | 62/293 |
| 2,779,195 | 1/1957 | Simon | 73/421 R X |
| 3,347,101 | 10/1967 | Kennedy | 73/421 R |
| 3,358,648 | 12/1967 | Berens | 62/293 X |

*Primary Examiner*—Daniel M. Yasich
*Attorney, Agent, or Firm*—M. Howard Silverstein; David G. McConnell

[57] ABSTRACT

A stream bed sediment sampler easily obtains a nearly undisturbed, stratified sample containing stream gravel, intergravel water, and organic material. The temperature of a probe inserted into the sediment is quickly reduced to a point where the material immediately surrounding the probe freezes and clings to the probe upon its removal from the stream bed. The equipment is inexpensive, easy to assemble, and portable.

7 Claims, 2 Drawing Figures

CRYOGENIC SEDIMENT SAMPLER

BACKGROUND OF THE INVENTION a. Field of the Invention

This invention relates to an apparatus for obtaining representative samples of sediment from stream beds, river beds, lake beds, and the like. More specifically, it relates to an apparatus containing a cryogenic probe which freezes portions of stream beds (the term "stream beds" will be used herein to include river beds, lake beds, and the like). These frozen portions cling to the probe and are easily removed from their environment.

b. Description of the Prior Art

Determining the effects of industrialization, mining, farming, road building, logging, etc., on the surrounding environment is important in future planning of these and other vital industries. Of particular importance to the fishing industry are programs designed to detect environmental changes in streams, rivers, lakes, bays, etc., used by spawning salmon and the like. Many of these changes are small, and sensitive techniques are needed to detect them.

Apparatuses for sampling stream bed sediments described in the literature have not generally been adequate.

One such device consists of an open-ended tube surrounded by a closable, cooling jacket into which is placed dry ice and n-butyl alcohol. The device containing the coolant is allowed to settle into the muddy sediment at the bottom of a lake. After several minutes the device containing the frozen core is lifted to the surface (J. Shapiro, Ecology, Vol. 39, No. 4, p. 758, 1958).

Another type of sediment sampler, which circulates acetone, chilled with dry ice, through a probe immersed in a stream bed, requires 1¼ to 2 hours and 12 to 14 Kg. of dry ice to freeze a core 18 to 25 cm. in diameter and 35 cm. long (N. H. Ringlu, Master of Science Thesis, Oregon State University, June 1970).

A piston type device for sampling surface sediments of lake bottom deposits has also been described (S. R. Brown, Ecology 37: 611–613, 1956).

A predecessor of the instant invention was described by me in a U.S.D.A. Forest Service Research Note, PNW-205, August 1973, Forest Service, U.S. Department of Agriculture, Portland, Oregon. This prior art sediment sampler consisted of a ½ to ¾ inch hard-drawn copper pipe 3 feet in length with a point machined from brass soldered to one end and closing the pipe. Another pipe of ⅜ inch soft-drawn copper, cut to reach to the bottom of the first pipe, was connected to a wire reinforced $CO_2$ delivery hose with brass fittings. The $CO_2$ delivery hose was connected through a ¼ inch NPT gate valve to a 15 to 20 pound fire extinguisher bottle. Even with the valve controlling $CO_2$ delivery through the smaller pipe, obtaining an even flow of gas was difficult, and the smaller pipe would jump out of the larger pipe (i.e., probe) when the valve was opened. It was necessary, therefore, to securely tie down the $CO_2$ delivery pipe. Also, the difficulty in controlling $CO_2$ delivery resulted in unequal cooling between samples so that time of sampling, and reproducibility varied substantially.

SUMMARY OF THE INVENTION

The sediment sampling apparatus of the invention comprises a first tube of heat-conducting material open at one end and closed at the other, a second tube open at one end and closed at the other having an outside diameter smaller than the inside diameter of the first tube and a length at least as long as the first tube. The second tube loosely fits inside the first tube so that the closed end of the second tube is in close proximity to the closed end of the first tube. A plurality of nozzles in an array is located near the closed end of the second tube. The nozzles are of a size which allows a controlled release of a gas under pressure from inside the second tube. Connected to the second tube is a means for delivering to the second tube a gas under a pressure sufficient to decrease the temperature of the gas to below the freezing point of water when the gas is released to the atmosphere through the nozzles.

The instant invention has several advantages over prior art devices.

1. Manifolding gas into the bottom of the probe using multiple nozzles in an array releases the gas to atmospheric pressure, offering thermodynamic advantages, at the proper location inside the probe, and eliminates the problem of the gas delivery tube jumping out of the probe.
2. The system is simpler because of the elimination of a valve and fittings. The nozzle array allows the system to operate at full tank pressure by controlling the gas release at a predetermined rate.
3. Full pressure operation lets the entire system, except the probe, operate at ambient temperature, greatly reducing the chance of component damage due to extreme thermal shock, keeps hoses flexible, reduces handling problems, and allows smaller size hoses and fittings to be used.
4. Having an easily controlled release of gas results in a more reproducible testing procedure.

DESCRIPTION OF THE PREFERRED EMBODIMENTS

Figures 1, 2:
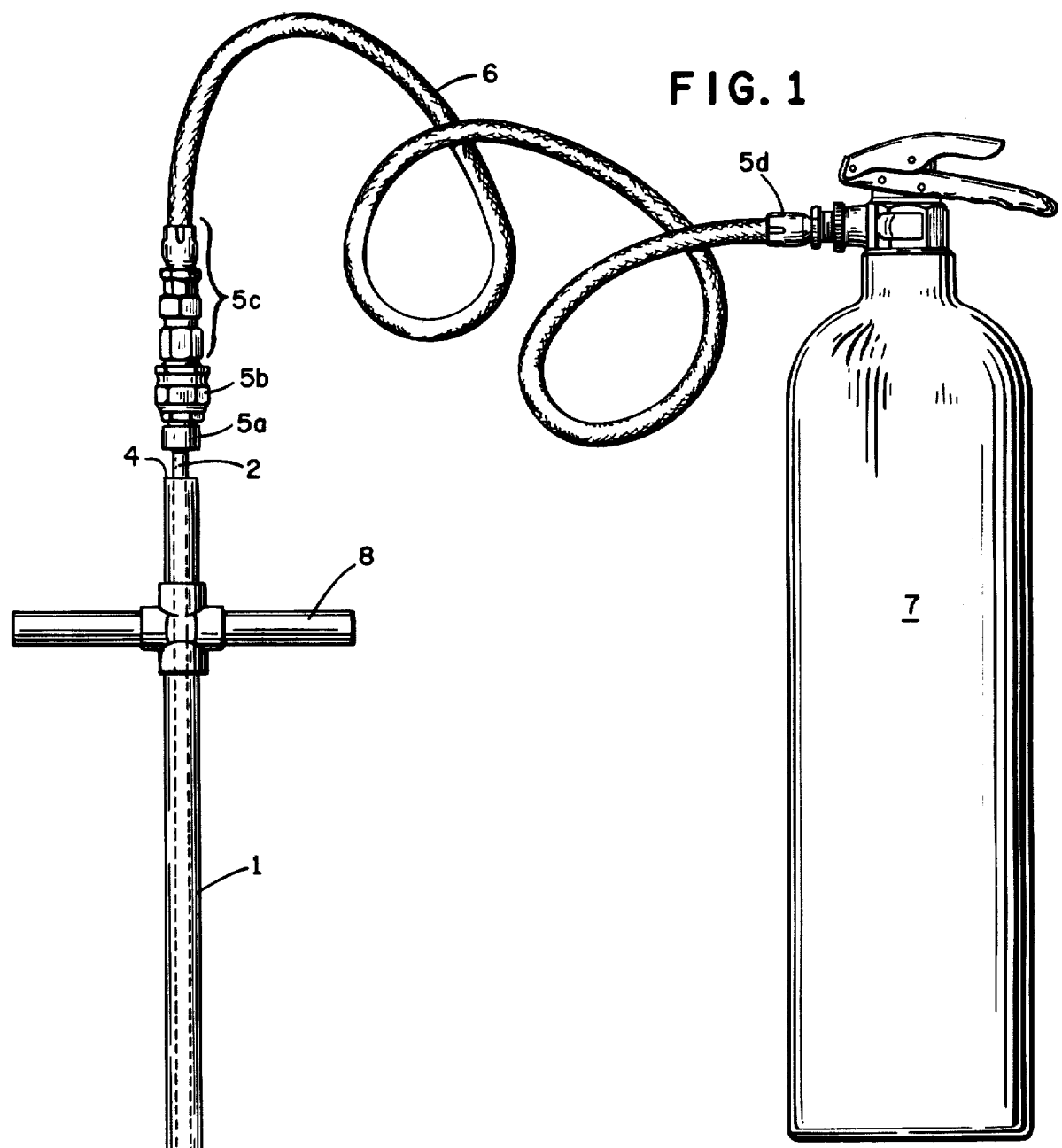
FIG. 1 is a view of a single embodiment of the invention with the lower portion of the probe cut away exposing the nozzle array on the gas delivery tube.
FIG. 2 is a section of the gas delivery tube showing the nozzle array.

The invention's value lies in its ability to reduce the sampling area disturbance to a minimum. The probe is inserted into a stream bed. The sample is then frozen and removed undisturbed as it was in the natural state. The resulting sample is easily handled and examined, and portions can be removed for analysis and testing, or preserved for future use. No loss of material including sub-micron fine silts, organic material, and water is experienced during sampling and handling. The equipment is simple to use, provides reproducible results, and is easily portable in the field without sacrificing the desirable features of good heat transfer, easy assembly, and reasonable equipment cost.

The figures depict a single preferred embodiment of the invention. Equivalents to the preferred embodiments described herein will be obvious to those skilled in the art and will be considered to be within the scope of the invention. FIG. 1 illustrates the assembled device. Probe 1 is a tube open to the atmosphere at opening 4 constructed from a heat-conducting material (e.g., copper pipe), and probe tip 10 which is fastened to probe 1 in any suitable manner (e.g., soldering, welding, or threading). Probe tip 10 fabricated from copper, brass, or other suitable rigid material, but preferably from steel. The lower thermal conductivity of steel causes a sharp cut off of the freezing at the bottom of the sample, and thereby aids in obtaining a sample that is more evenly shaped and less biased by differences in size over the length of the sample. However, in certain types of stream beds, such as, very loose gravel, a pointed probe tip is unnecessary. The length of probe 1 depends only on the depth of water in the stream bed being sampled, and on ease of handling. The preferable length is about 3 to 4 feet, and a preferable inside diameter is about 0.50 to 0.75 inch. It also is preferable to attach to probe 1 a means, such as handle 8, for forcing the probe into the stream bed and for removing it after freezing has been accomplished.

Gas delivery tube 2, shown in both FIGS. 1 and 2, can be made of any material in which nozzles 3 can be mounted, and which can withstand the gas pressures necessary to accomplish the intent of the invention. It is preferred, however, that the material be substantially non-heat conducting so that only probe 1 is at a temperature lower than ambient. The outside diameter of tube 2 is smaller than the inside diameter of probe 1 so that tube 2 fits loosely inside probe 1. Preferably gas delivery tube 2 has an outside diameter which is about 50 to 75% of the inside diameter of probe 1. For example, if probe 1 has an inside diameter of 0.50 inch, gas delivery tube 2 would have an outside diameter of from about 0.25 to 0.375 inch. Gas delivery tube 2 should have a length sufficient for its closed end to reach the bottom of probe 1. Connected to the upper end of gas delivery tube 2 is a means for delivering to tube 2 a gas under pressure. The gas delivery means includes items 5, 6, and 7 and will be discussed later.

FIG. 2 illustrates the lower section of gas delivery tube 2 showing the array of nozzles 3. As shown, nozzle 3a is located about 1 inch from the end of the tube, and nozzles 3a, 3b, 3c, and 3d are arranged as shown about 2 inches apart on 120° centers around tube 2. Many arrangements of the nozzles, other than the one shown, would be equivalent for the purposes of the invention. However, nozzles 3 should be in a sufficiently symetrical array to give stability to tube 2 and to prevent tube 2 from jetting out of tube 1 when the gas pressure is turned on. When a liquid $CO_2$ fire extinguisher is the source of gas used in the invention, it is preferred that nozzles 3 have holes of about 0.006 inch in diameter which allows the gas to be released to the atmosphere at a flow of about 0.2 pound of $CO_2$ per minute at a temperature of about $-78°$ C.

Cap 9 closes off the end of tube 2 and is pressure tight. It can be attached by any suitable method (e.g., welding or threading).

The gas delivering means, shown in FIG. 1 includes pressurized gas vessel 7, a length of pressurized tubing 6, and connectors 5a–d for connecting the pressure tubing to pressure vessel 7 and to gas delivery tube 2. A means for opening and closing the gas pressure is usually included on gas vessel 7. Preferred pressurized gas vessel 7 is a 15 or 20 pound fire extinguisher, which contains liquid $CO_2$ under about 800 psi. Other types of containers and other gases which are suitable for use in accordance with the invention will be known to those skilled in the art. The main criteron being the ability of the gas to achieve a temperature drop, when released to the atmosphere inside probe 1, sufficient to cause the water to freeze in the stream bed immediately surrounding the probe. Pressure tubing 6 obviously must withstand the same gas pressure as vessel 7. A 3/16 inch medium pressure wire reinforced cloth covered hose is preferred because this type of hose maintains good flexibility when used with liquid $CO_2$ fire extinguishers. Any type of fittings known in the art as pressure fittings can be used for connectors 5a–d. Connector 5b is a connector which contains a 10 micron filter. The use of a suitable filter in the gas line nearly eliminates any of the plugging that plagues the prior art apparatuses (see PNW 205, supra). Connector 5b and the filter are preferred parts of the invention, but they are optional.

Having described my invention, I claim:

1. An apparatus for sampling the sediment compositions of stream beds and the like comprising,
   a. A first tube of heat-conducting material open at one end and closed at the other end, the open end being open to the atmosphere;
   b. A second tube open at one end and closed at the other end having an outside diameter smaller than the inside diameter of said first tube and a length at least as long as said first tube, said second tube loosely fitting inside said first tube so that the closed end of said second tube is in close proximity to the closed end of said first tube;
   c. A plurality of nozzles of a size which allows a controlled release of a gas under pressure from inside said second tube, said nozzles being located near the closed end of said second tube in a sufficiently symmetrical array so that said second tube remains stable within said first tube when the gas is released to atmospheric pressure within said first tube;
   d. A means connected to the open end of said second tube for delivering to said second tube a gas under pressure sufficient to decrease the temperature of said gas to below the freezing point of water when said gas is released through said nozzles to the atmosphere in said first tube thereby quickly decreasing the temperature of said first tube to below the freezing point of water in the stream beds and the like into which said first tube is inserted.

2. An apparatus as described in claim 1 wherein the heat-conducting material of the first tube is copper.

3. An apparatus as described in claim 1 wherein the closed end of the first tube is closed with a pointed steel tip.

4. An apparatus as described in claim 1 wherein the first tube has a handle means attached near the open end for facilitating said first tube's insertion and removal from the stream bed.

5. An apparatus as described in claim 1 wherein the inside diameter of the second tube is about 50 to 75% of the inside diameter of the first tube.

6. An apparatus as described in claim 1 wherein the means for delivering to the second tube a gas under pressure is a carbon dioxide fire extinguisher connected to said second tube through pressure tubing.

7. An apparatus as described in claim 1 wherein:
   a. the first tube is a 3 to 4 foot copper pipe having an inside diameter of from ½ to ¾ inch;
   b. the second tube is a 3 to 4 foot steel tubing having an inside diameter of about ¼ inch;
   c. the nozzles, which have 0.006 inch diameter holes, are located on 120° centers about 2 inches apart with one hole about 1 inch from the closed end of the second tube;
   d. the means for delivery to the second tube a gas under pressure is a carbon dioxide fire extinguisher connected to said second tube through a 3/16 inch inside diameter medium pressure wire-reinforced cloth-covered hose by means of suitable couplings, one of said couplings containing a 10 micron in-line filter for reducing plugging of the tubes during use.

* * * * *